(12) United States Patent
Perez Ballesta

(10) Patent No.: US 10,024,769 B2
(45) Date of Patent: Jul. 17, 2018

(54) DIFFUSIVE SAMPLING DEVICE

(71) Applicant: THE EUROPEAN UNION, REPRESENTED BY THE EUROPEAN COMMISSION, Brussels (BE)

(72) Inventor: Pascual Perez Ballesta, Angera (IT)

(73) Assignee: THE EUROPEAN UNION, REPRESENTED BY THE EUROPEAN COMMISSION, Brussels (BE)

( * ) Notice: Subject to any disclaimer, the term of this patent is extended or adjusted under 35 U.S.C. 154(b) by 94 days.

(21) Appl. No.: 14/442,809

(22) PCT Filed: Nov. 13, 2013

(86) PCT No.: PCT/EP2013/073765
§ 371 (c)(1),
(2) Date: May 14, 2015

(87) PCT Pub. No.: WO2014/076153
PCT Pub. Date: May 22, 2014

(65) Prior Publication Data
US 2015/0300928 A1    Oct. 22, 2015

(30) Foreign Application Priority Data

Nov. 14, 2012 (EP) ..................................... 12192678

(51) Int. Cl.
G01N 1/22 (2006.01)
(52) U.S. Cl.
CPC ......... G01N 1/2273 (2013.01); G01N 1/2214 (2013.01); *G01N 2001/2276* (2013.01); *G01N 2001/2285* (2013.01)

(58) Field of Classification Search
CPC ... G01N 2001/2285; G01N 2001/2276; G01N 1/2214; G01N 1/2273
(Continued)

(56) References Cited

U.S. PATENT DOCUMENTS 4,158,958 A * 6/1979 Braun ................ G01N 33/0011
422/88
4,350,037 A * 9/1982 Higham ............... G01N 1/2273
422/88
(Continued)

FOREIGN PATENT DOCUMENTS

CN    101852692 A  * 10/2010
EP       2063248 A1 *  5/2009 ........... G01N 1/2214
(Continued)

OTHER PUBLICATIONS

Translation EP 2063248 Granet.*
(Continued)

*Primary Examiner* — Natalie Huls
*Assistant Examiner* — Monica S Young
(74) *Attorney, Agent, or Firm* — Cantor Colburn LLP

(57) ABSTRACT

A diffusive sampling device (1) comprises a porous hollow diffusion body (3) removably held on a support body (2), an adsorbent body (4) located inside said diffusion body (3), wherein the hollow diffusion body (3) has a cylindrically shaped wall with an upper section comprising a closed upper end and a distal lower section comprising an open lower end and wherein the diffusion body (3) is held on the support body (2) by means of one or more o-rings (7) fixed to its lower section, wherein the adsorbent body (4) is kept in a predetermined place inside the upper section of the diffusion body (3) by way of an elastic means, such as a spring (6). The use of such devices as well as a method for air sampling and monitoring.

15 Claims, 9 Drawing Sheets

(58) Field of Classification Search
USPC .................................................. 73/863.23
See application file for complete search history.

(56) References Cited

U.S. PATENT DOCUMENTS

| | | | |
|---|---|---|---|
| 7,559,980 B2 * | 7/2009 | Guild | G01N 1/2273 422/88 |
| 2002/0148355 A1 | 10/2002 | Smith et al. | |
| 2003/0215958 A1 * | 11/2003 | Kin | G01N 1/2273 436/181 |
| 2006/0137689 A1 * | 6/2006 | Evensson | A62B 23/06 128/205.27 |
| 2008/0028933 A1 * | 2/2008 | Ross | B01D 53/0415 95/138 |
| 2012/0222555 A1 * | 9/2012 | Gupta | B01D 53/0438 95/136 |

FOREIGN PATENT DOCUMENTS

| | | | | |
|---|---|---|---|---|
| JP | H10300647 A | | 11/1998 | |
| JP | 2001004609 A | * | 1/2001 | |
| JP | 2002357517 A | | 12/2002 | |
| JP | 2003185541 A | | 7/2003 | |
| JP | 2005510708 A | | 4/2005 | |
| WO | 0016063 A1 | | 3/2000 | |
| WO | 2008015031 A1 | | 2/2008 | |
| WO | WO 2008015031 A1 | * | 2/2008 | G01N 1/2214 |

OTHER PUBLICATIONS

Translation CN 101852692 Li.*
Translation JP 2001004609 A.*
Daniela Buzica et al. "Modelling of the uptake rate of the nitrogen dioxide Palmes diffusive sampler based on the effect of environmental factors", Journal Environ. Monit., The Royal Society of Chemistry Feb. 2005, vol. 7, No. 2, pp. 169-174.
Foday M. Jaward et al. "Passive Air Sampling of Polycyclic Aromatic Hydrocarbons and Polychlorinated Naphthalenes Across Europe", Environmental Toxicology and Chemistry, 2004, vol. 23, No. 6, pp. 1355-1364.
International Preliminary Report on Patentbility dated Oct. 29, 2014 re: Application No. PCT/EP2013/073765; citing: U.S. Pat. No. 4,350,037 A, EP 2 063 248 A1 and WO 2008/015031 A1.
International Search Report dated Mar. 3, 2014 re: Application No. PCT/EP2013/073765; citing: U.S. Pat. No. 4,350,037 A, EP 2 063 248 A1, WO 2008/015031 A1, US 2003/215958 A1, WO 00/16063 A1, US 2002/148355 A1 and U.S. Pat. No. 4,158,958 A.
Written Opinion dated Mar. 3, 2014 re: Application No. PCT/EP2013/073765; citing: U.S. Pat. No. 4,350,037 A, EP 2 063 248 A1, WO 2008/015031 A1 and US 2003/215958 A1.
Chinese Office Action dated Aug. 17, 2016 re: Application No. 201380055534.8; pp. 1-24; citing: CN 101852692 A, U.S. Pat. No. 4,350,037, CN1492223A, WO2008/015031A1, CN101126686A, CN101852691A.
JP Office Action dated Sep. 21, 2016 re: Application No. P2015-541192; pp. 1-10; JP P2002-357517A, U.S. Pat. No. 4,350,037, JP P2001-004609A, WO2008/156199, JP P2005-510708, JP P2003-185541A and JP PH10-300647A.

* cited by examiner

DIFFUSIVE SAMPLING DEVICE

TECHNICAL FIELD

The present invention generally relates to diffusive sampling of organic compounds and vapors from ambient air, such as for air quality monitoring, etc. In particular, the invention concerns a new diffusive sampling device, as well as its use and a method for collecting samples using said device.

BACKGROUND ART

There are two main ways to achieve air and vapor sampling. On the one hand, the active sampling, which requires physical drawing of a volume of air through a collection medium by means of a suction pump. On the other hand, the passive sampling, in which the collection is achieved thanks to an adsorbent material. The present invention relates to the field of passive air sampling, also called passive diffusive sampling.

Passive diffusive sampling relies on the diffusion of analytes through a diffusive surface onto an adsorbent. After sampling, the analytes are chemically desorbed by solvent extraction or thermally desorbed and analyzed. Passive sampling does not involve the use of heavy and encumbering pumping systems, is not impacted by power disruptions, does not require extensive supervision, is quiet, non-flammable and does not represent an explosion hazard. It can be performed by anyone, anywhere and at a very low cost. Moreover, it is not susceptible to sample breakthrough, a common problem associated with active sampling performed with an air pump.

The passive sampling allows the analyte to be collected owing to the concentration gradient between the bulk ambient air concentration and a retention medium (i.e. solid adsorbent, liquid or gel absorbent). That means that the up-take or sampling rate of a device will depend on the compound (diffusivity), area and length of diffusion (i.e. design parameters, short of diffusion or permeation media), and adsorbent characteristics (adsorption isotherm). Parameters like adsorption isotherm, adsorption capacity, sampling rate and variables like concentration level and sampling time are correlated, in such a way, that for instance, high concentrations of analyte in ambient air will saturate the adsorbent and decrease its sampling rate; in a similar way, a high sampling rate will more quickly saturate the adsorbent, although would allow higher sensitivity and shorter sampling times. Longer sampling times may cause similar saturation effects.

In practice, the sampling rate that applies to a diffusive sampler is valid for a particular analyte-adsorbent combination over a certain range of concentration and sampling time.

The uptake rate of a diffusive sampler depends on its design: length and resistance along the diffusion path from ambient air to the adsorbent bed. Most of the diffusive samplers have been designed for a specific application, which provide sampling rates that are sometimes very low or very high to prevent the saturation of the adsorbent or its use for longer times or vice versa.

Some diffusive samplers contain diffusion membranes and even if they are re-useable, they can easily deteriorate with time, becoming dirty with graphitized adsorbent or by exposure to ambient conditions. The possibility of cleaning is limited as the membranes cannot be separated from the sampler.

The material of the diffusive sampler is sometimes a handicap for the measurement of certain compounds, which can contaminate the sample or act as a competitor for adsorption.

The transport, storage and interruption of the sampling for a certain period of time (for instance for interrupted cumulative personal sampling) is difficult, to handle as the sample may easily become contaminated.

This explains the diversity of designs, adsorbents and variations of diffusion samplers on the market. Each diffusive sampler, in principle, has been designed for a particular application; i.e. short or long term sampling time, different environment (workplaces, ambient air, indoor air, and personal exposure), different compounds, analytical techniques and levels of concentration. Documents U.S. Pat. No. 4,350, 037, EP 2 063 248, WO 2008/015031, US 2003/0215958 describe several different kinds of diffusive samplers. Nevertheless, some of these samples are used in different fields, under different sampling conditions; which may affect an optimized performance of the diffusive sampler, where its operational conditions are limited by design to a certain range.

BRIEF SUMMARY

The present invention provides a more versatile diffusive sampling device, also called diffusive sampler, which allows to reliably collect analytes over variable periods of time in variable (fixed or mobile) locations. The sampler should be sensitive, yet easy to manipulate even by less experienced users.

In order to overcome at least some of the above-mentioned disadvantages and problems associated with existing solutions, the present invention proposes a diffusive sampling device comprising a porous hollow diffusion body removably held on a support body with an adsorbent body located inside said diffusion body. The hollow diffusion body has a cylindrically shaped (porous) side-wall with an upper section comprising a closed (but also porous) upper end (top-wall) and a distal lower section comprising an open lower end and wherein the diffusion body is held on the support body by means of one or more toric joints or o-rings fixed to its lower section. The adsorbent is preferably kept in a predetermined place inside the (upper section of the) diffusion body by way of elastic means, such as a spring or similar.

The main advantages of the proposed solution are that the device is easy to assemble and to manipulate; it does require only few manufacturing steps, which reduces the manufacturing costs to a minimum. Furthermore, it maximizes its sensitivity by combining both radial and axial adsorption, thereby allowing for compact dimensions without compromising on performance (see also experimental data below).

Indeed, the dimensions of the hollow diffusion body may be very compact; generally a length L from the lower to the upper end of the diffusion body between 10 to 30 mm, preferably of 15 to 25 mm, is sufficient. The outer diameter ($D_o$) of the diffusion body is typically comprised between 6 and 25 mm, preferably even from 7.0 to 15.5 mm. The thickness of the diffusion body's (side and top) walls usually ranges from 1 to 7 mm, preferably from 1.5 to 3.5 mm. In a particularly preferred embodiment, the hollow diffusion body has a length L of 20.0±0.3 mm, an outer diameter $D_o$ of 8.0±0.3 mm, and a wall thickness $T_W$ of 2.0±0.2 mm.

As a consequence of such a compact design, the diffusive sampling device is easily transportable, simple to use and to position in the desired location. Furthermore, it fits to conventional desorption equipment.

The removable hollow cylindrical diffusion body, which is made of a porous material, preferably integrally molded, sintered or machined, can be easily interchanged in order to select a porosity in accordance with the compounds that have to be sampled. It can be made of several different materials (stainless steel, bronze, PTFE, polypropylene or even catalytic materials for sampling of reactive compounds). "Porous" designates the fact that the material of the hollow cylindrical diffusion body allows the circulation of the compounds to be sampled between the inside and the outside of the hollow cylindrical diffusion body without requiring a specific opening within its structure. It means that the compounds to be sampled can passively circulate (be exchanged) through the pores of the hollow cylindrical diffusion body and thus through at least a major part of the surface of the hollow cylindrical diffusion body or even the whole surface of the hollow cylindrical diffusion body. In this way, the sample to be tested can come into contact with the adsorbent body. Moreover the diffusion body can be easily separated from the support and adsorbent body and easily chemically or thermally cleaned for further sampling without risking damages. The external cylindrical shape of the diffusion body allows for both radial and axial adsorption, providing a relatively important exchange surface with respect to the volume of the diffusion body.

These porous diffusion bodies may be provided with different porosities, different pore sizes and different pore size distributions, depending on the particular application and analyte(s) to be sampled. The overall porosity of diffusion body is generally chosen between 5 and 70%, preferably between 10 and 50%, still more preferably between 20 and 45%. The (mean) pore size or pore diameter will usually be from 0.25 to 100 µm, preferably 0.5 to 60 µm, e.g. 0.5, 1, 3, 5, 8, 10, 20, 30, 40, 50 or 60 µm. Preferably, the pore size distribution is chosen to be narrow around the desired mean pore diameter, more preferably the standard deviation of the average pore size is at most 10%.

The diffusive sampling device preferably comprises one or more, e.g. one or two grooves machined or otherwise formed at the outer side of the lower section of the diffusion body which allows for receiving a corresponding number of o-rings to keep the diffusion body (removably, yet firmly) attached to the support body and thereby efficiently preventing any sliding of the diffusion body in its attached position.

Alternatively or additionally to the embodiment described above, the diffusive sampling device may also be conceived to integrate one or more similar grooves at the inner side of the upper section of the support body to keep the diffusion body removably attached thereto.

Furthermore, as the sampling device can be provided with a series of different diffusion bodies having different porosities, a preferred embodiment comprises the use of two o-rings to attach the diffusion body to the support body in which the porosity of the diffusion body can be codified according to a color combination of the two o-rings (for example as shown in Table 1). The same code can be used for devices having more than two o-rings, e.g. by considering only the color of the two lower o-rings (o-rings closest to the open lower end of the diffusion body). Of course, this code can be completed for embodiments with more different porosities; also for embodiments with 1 o-ring the code can be adapted by the use of additional colors. If desired, the exemplified code can be extended by using additional colors and/or additional o-rings.

TABLE 1

Example of codification for the diffusion body porosity (2 o-rings)

| | Pore size, µm | | | | | |
|---|---|---|---|---|---|---|
| Stainless Steel | 0.5 | 1 | 3 | 5 | 10 | 20 |
| o-ring upper | Black | Green | Red | Black | Green | Red |
| o-ring lower | Black | Black | Black | Green | Green | Green |

| | Pore size, µm | | |
|---|---|---|---|
| Bronze | 8 | 20 | 60 |
| o-ring upper | Green | Red | Black |
| o-ring lower | Green | Green | Red |

| | Pore size, µm | | | | | |
|---|---|---|---|---|---|---|
| PTFE | 5 | 10 | 20 | 30 | 40 | 50 |
| o-ring upper | Black | Green | Red | Black | Green | Red |
| o-ring lower | Green | Green | Green | Red | Red | Red |

The adsorbent body can be easily cleaned up, e.g. with solvent or short temperature treatments, and hence reused. The adsorbent body is lodged inside and against the hollow core or bore of the hollow cylindrical diffusion body and maintained at the top of the diffusion body (i.e. in the upper section against the upper end) thanks to elastic means, advantageously a spring (preferably made of an inert material, such as stainless steel), thus not only allowing for an optimal actual adsorption surface, but also for a reliable positioning and hence reproducible measurements.

The adsorbent material of the adsorbent body may be selected among any appropriate material having a high specific surface area capable of physically or chemically bonding an analyte to its surface. Examples of appropriate materials are silica gel, silicone, zeolites, (activated) carbon, graphite charcoal (carbopacks, carbotraps, tenax, chromosorb, etc.). The adsorbent body may be either a mono-block or cohesive piece of adsorbent or it may comprises a particulate adsorbent inside a perforated container, such as a stainless steel mesh, a modified spring or double spring, a porous material that contains a particular reactive agent, an adsorbent paper or a bag container made of a permeation membrane with a liquid absorbent inside or any combination thereof.

In practice, the diffusive sampling device can be loaded with different types of adsorbents depending on the compound(s) to be sampled and analyzed. These may vary from rubber (silicone or Silastic®) to graphitized charcoal (i.e., active charcoal, carbopack-B, carbopack-X, carbopack-C). They can be compacted as a unique solid piece (monoblock) or in granule or powder form with a defined mesh size that could range from 20 to 100 mesh size. Typical adsorbents are carbopack-X (40-60 mesh), carbopack-B (20-40 mesh), tenax GR (40-60 mesh), tenax TA (60-80 mesh) or silica (40-60 mesh), which can be impregnated with appropriated reactive agent(s) for adsorption and analysis of a particular analyte. This provides the possibility of sampling a wide range of compounds from inorganic (as $NO_2$, $O_3$, $NH_3$) to organic nature (HC, VOC, PAHs).

In a preferred embodiment, the adsorbent container is a so-called double spring container and comprises (at least) two springs of different length and dimensions with one conically closed end that can be screwed one inside the other. The adsorbent itself is inserted within this double spring container either as a particulate adsorbent or a monoblock (rigid) adsorbent.

For rigid adsorbents such as a rod of silicone (i.e. 13 mm×3 mm inner diameter), this can be directly rolled up inside the long spring container up to the closed end. Thereafter, the short spring cap can be screwed down inside the long spring until the whole length of the container is e.g. 20 mm.

In this way, the adsorbent is more easily manipulated, avoiding possible contaminations with the walls of the diffusion body or any other component, due to the protection provided by the double spring container. The double spring container may be easily taken out from the diffusion body for analysis, such as by way of introducing it into a thermal desorption system.

In addition, this double spring container provides a sufficient resistance, when it is enclosed inside the diffusion body and it keeps the adsorbent steady inside; thereby improving the reproducibility and performance of the diffusion process.

When the adsorbent is a particulate matter (such as a powder), the adsorbent is previously arranged inside of a cylindrical tube, such as in a stainless steel Dutch twill weave (16 mm×29 mm outer diameter) with an appropriated nominal light smaller than the corresponding mesh size of the adsorbent (i.e. for 20-40 mesh, a 5 µm nominal light is sufficient). Both end sides of the cylindrical tube can be closed e.g. with a piece quartz filter of 3 mm of diameter.

The cylindrical tube in twill weave containing the adsorbent may then be introduced inside of the double spring container, which is rolled up along the cylinder and closed at the open end with the short spring cap. A fixed number of rounds of the spring is distributed at equidistance along the cylinder and the final length is fixed at 20 mm.

Again the long spring container is acting as a protection of the cylindrical tube in stainless steel, thereby minimizing the formation of micro-particles and adsorbent losses.

The cross-sectional shape and dimensions of the adsorbent body are selected to closely match those of the hollow interior of the diffusive body, whereas the length of the adsorbent body is generally smaller than that of the interior of the diffusive body to allow for the insertion an elastic means, such as a spring (see above).

In a further aspect, the diffusive sampling device also comprises a cover to close the device. In the closed state, the cover is removably attached to the support body and thus encloses said hollow diffusion body. This generally hollow cylindrical cover avoids contamination of the sampler during transport, storage and other interruptions of the sampling and is easily put over the diffusion body and attached in an airtight manner to the support body, preferably by means of one or more o-rings (toric joints) between the support body and the cover (see below). The cover may be made of any appropriate material, such as metal or plastic, preferably it is made of polytetrafluoroethylene (PTFE) or aluminum. It should be noted that the cover is not only useful as a protection and conservation means, but may also be used for sequencing the sampling process, as will be described more in detail below.

In a particularly preferred example of diffusive sampling device, the cover is designed such that its hollow interior closely matches the outside shape of the diffusion body, thereby reducing the so-called dead volume inside the closed device. In other words, the inter-space between the cover and the diffusion body is preferably minimized in order to attenuate possible back-diffusion during storage or transport. In practice, the inside diameter of the cover is generally chosen to be 4 to 20% larger than the outside diameter of the diffusion body. The reduction of the open volume inside the closed device reduces indeed the desorption of the collected compounds/analytes inside the closed device.

In a still further embodiment of the device described herein, the cover further comprises a non-return valve to avoid over-pressure when the sampler is closed and to allow the hermetic closure of the sampling device. The non-return valve may be integrated to the cover and/or the support body, preferably however it is inserted on the top of the cover. Such a modified device can thus be closed under vacuum by eliminating the inside air through the aperture where the non-return valve is located. This non-return valve also allows the expulsion of the air that over-pressurizes when closing the device. Such air flow ejection advantageously requires a minimum activation pressure (overpressure) to open the valve, for example from 1 to 10 kPa, such as about 4 kPa.

The support body may be made of any appropriate material, such as metal or plastic, preferably it also has a roughly cylindrical shape and is advantageously provided with an external upper surface (upper section) and an external raised lower surface (raised lower section with a larger diameter) to facilitate the opening of the diffusive sampling device. In a further embodiment, a split or peripheral depression is arranged in the raised lower surface allowing for the attachment of the sampling device to an additional holder, either with the cover applied or not.

In a further embodiment, the diffusive sampler thus further comprises a holder which is removably attached to a peripheral depression arranged in the raised lower surface of the support body. The holder can be used to fix the sampling device in any desired orientation to variable locations and to avoid accidental falls, such as due to movements during personal exposure sampling. The holder may be of any appropriate type, such as a metal or plastic clip, a screw or a magnetic piece placed at the base of the support body. In one embodiment for mobile or personal use, it comprises a cut profile in plastic material that allows it to be closed around the diffusion body (see FIGS. 5A and 5B). Such a holder looks like a sort of tweezers that, when closed, draws a circular shape that fits on the groove of the diffusion body. Other embodiments for stationary ambient sampling may comprise a metal clip with a (disposable) protective screen.

In a further embodiment, one or more, preferably one outer groove is machined in the upper section of support body to receive the appropriate number of o-rings (toric joints) that provide for an airtight closure between the support body and the cover. It is to be noted that the support body is preferably made of stainless steel and comprises one or more o-rings made of an inert rubber, to avoid contamination of the sample.

In view of the above, the multiple advantages of the diffusive sampling devices (samplers) described herein can be summarized as follows:

The relative surface for diffusion with respect to the adsorbent is greater than that for the other commercially available models. In the present samplers there is a combination of radial and axial diffusion. Nevertheless, this ratio can be modified by interchanging the diffusion body.

The diffusion body is interchangeable by diffusion bodies with other total porosities (e.g. 10-50%), pore sizes (e.g. 0.5-60 µm), pore size distribution and material (stainless steel, bronze, PTFE, polypropylene or catalytic (ozone scrubber) materials for sampling of reactive compounds). This provides a dynamic range for diffusion, which allows for the selection of the appropriate diffusion resistance according to the application (outdoor, indoor, ambient air), pollutant and integrated sampling time.

The amount of adsorbent has been reduced compared to known solutions with the consequent reduction in the blank level and the cost of the sampler.

Furthermore, the herein described samplers are easier to clean up with shorter temperature treatments needed. Therefore, the decrease in sensitivity due to the lower overall amount of analyte collected with respect to other diffusive samplers with greater weight of adsorbent is compensated by the decrease in the detection limit due to the improvement of the blank level of the adsorbent.

The adsorbent body fits to most of the thermal desorption systems on the market.

The diffusion body is re-usable. This can be chemically and thermally cleaned independently of the rest of the sampler. This improves the life cycle, removes drifts of the sampling rate with time and keeps low blank levels.

The sampler can be directly opened for sampling and hermetically sealed for storage without any particular manipulation of the device and without causing an increase in the blank levels due to emissions from the construction material.

In a further aspect, the invention also encompasses the use of the herein described diffusive sampling devices for passive air monitoring over a large range of time periods. Furthermore, the invention also encompasses the use of the herein described diffusive sampling devices in stationary, mobile and personal exposure applications.

In a still further aspect, the invention also concerns a method for air monitoring using a diffusive sampling device as described herein, comprising the following steps: placing the device in a desired stationary or mobile location, optionally by attaching the device in said location using a holder, starting the sampling period by removing the cover from the support body, letting adsorption occur for a determined period of time and closing the device by replacing the cover on the support body after said period lapsed. In a variant of this method, the sampling period may be composed of a sequence of a number of periods of time, each separated by the closing of the device as described herein.

The closed diffusive sampling device may then be transported and transferred to an analyzing and measuring step comprising the introduction of the adsorbent body into a conventional desorption equipment provided with an analyte detection and measuring device, using any appropriate method to quantify the analyte(s) adsorbed in the sampler.

For analytical purposes, the method may include the use of blank samplers (diffusive samplers that are kept closed during the sampling to be analyzed in the same batch as the exposed samples) or the use of diffusive samplers in which the adsorbent has been previously marked e.g. with a deuterated internal standard (this is particularly interesting in case of PAH sampling followed by thermal desorption, gas-chromatography and mass spectrometry detection).

BRIEF DESCRIPTION OF THE DRAWINGS

Preferred embodiments of the diffusive sampling devices of the invention will now be described, by way of example, with reference to the accompanying drawings in which.

Further details and advantages of the present invention will be apparent from the following detailed description of several not limiting embodiments with reference to the attached drawings, as well as from the experimental data provided.

DESCRIPTION OF PREFERRED EMBODIMENTS

Figure 1:
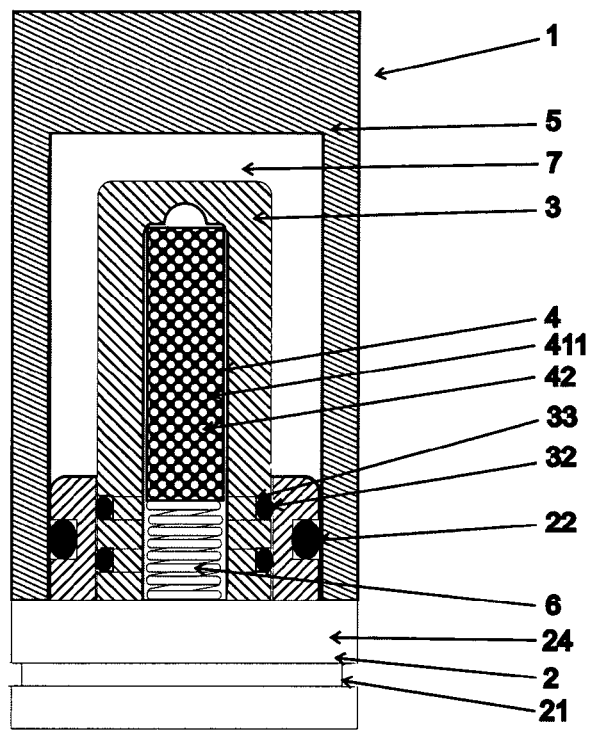
FIG. 1 is a cross sectional view of a first embodiment of the diffusive sampling device of the invention.

FIG. 1 represents a cross-section of first embodiment of a diffusive sampling device 1, comprising a support body 2, a diffusion body 3, an adsorbent body 4 and a cover 5 removably attached to an upper section of the support body 2 by means of o-ring 22 inserted into a groove 23 arranged on the outside surface of the upper section of the support body 2. The support body 2 also comprises a lower section with a raised surface 24 compared to the upper section, the lower section comprising preferably a peripheral depression or slit 21, e.g. for attaching a holder (not shown in FIG. 1).

The hollow diffusion body 3 is porous and essentially has a cylindrical shape with an upper section having a closed top end and a lower section with an open-ended bottom to insert an adsorbent body 4 inside the hollow interior of the diffusion body 3. The adsorbent body 4 comprises a particulate adsorbent 42 within a perforated container 411 and is held in place by means of a spring 6 when the diffusion body 3 is attached with its lower section to the support body 2. As an alternative, the adsorbent body 4 could also be a rigid, mono-block adsorbent 42, i.e. without container. In its lower section, the diffusion body comprises one or more, preferably two o-rings 32 arranged in corresponding grooves 33 located on the outside of the diffusion body 3.

Inside the closed sampling device, i.e. the diffusive sampling 1 comprising cover 5, a so-called dead volume 7 remains between the interior of the cover 5 and the outside of diffusion body 3.

Figure 2:
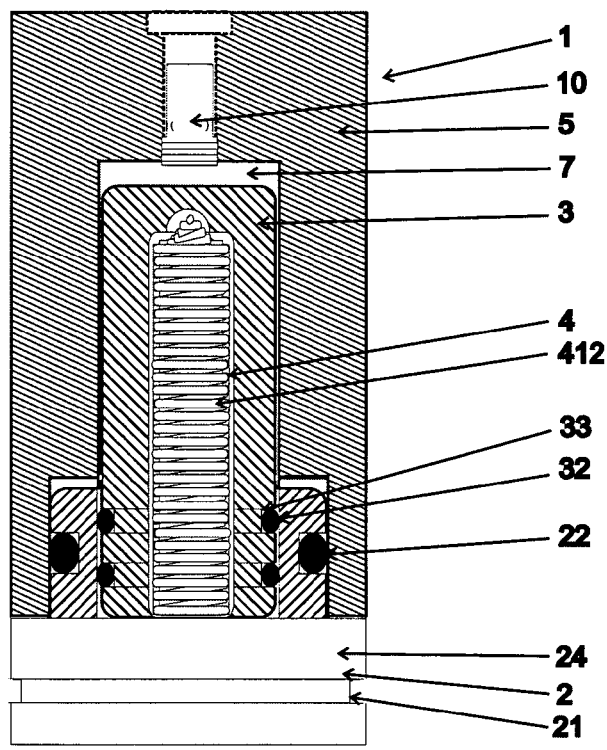
FIG. 2 is a cross sectional view of a second embodiment of the diffusive sampling device of the invention.

In FIG. 2, a second embodiment is represented comprising corresponding features, although in this embodiment adsorbent body 4 comprises a so-called double spring container 412 containing the particulate adsorbent 42 (not shown). The double spring container does not require a separate spring 6 as shown in FIG. 1. As an alternative, the adsorbent body 4 could also be a rigid, mono-block adsorbent 42, i.e. without container, held in place by means of a spring 6 as shown in FIG. 1. This second embodiment of the diffusive sampling device further comprises a non-return valve 10 arranged in the top end wall of the cover 5. Furthermore, said cover 5 has the particularity that its interior shape has been more closely matched to the outside shape of the adsorbent body 3 to minimize the dead volume 7 inside the closed device and thereby reducing back-diffusion of the adsorbed analytes. A double spring adsorbent container as presented in FIG. 2 allows for the arrangement of minimal amounts of adsorbent, such as e.g. Tenax GR (22-23 mg), Carbopack-X (33-35 mg) or silicone rod (10 mg).

Figure 3:
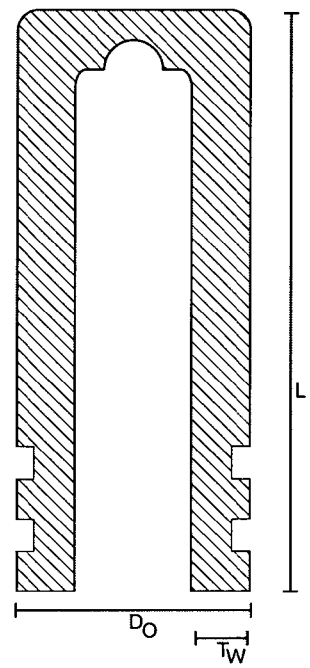
FIG. 3 is a cross sectional view of a diffusion body useable in a diffusive sampling device of the invention.

FIG. 3 represents a cross-section of the diffusion body 3 only with length L, outer diameter $D_o$ and wall thickness $T_w$. In a particularly preferred embodiment, L is 20 mm, $D_o$ is 8 mm and $T_w$ is 2 mm.

Figure 4:
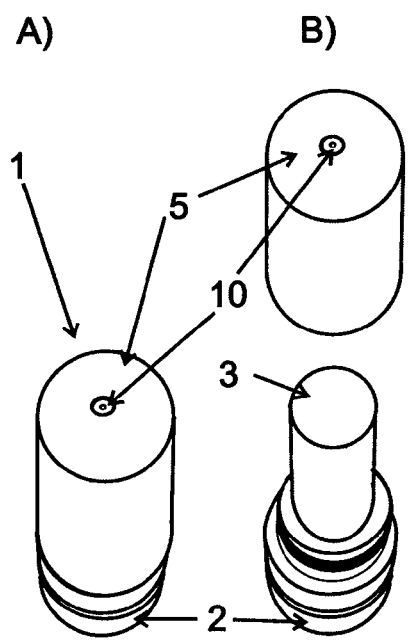
FIGS. 4A and 4B are perspective views of an embodiment of a diffusive sampling device of the invention (closed and open)

FIGS. 4A and 4B show an embodiment of a sampling device 1, once closed with the cover 5 mounted over the diffusion body 3 to the support body 2 and once with the cover 5 removed for sampling.

Figure 5:
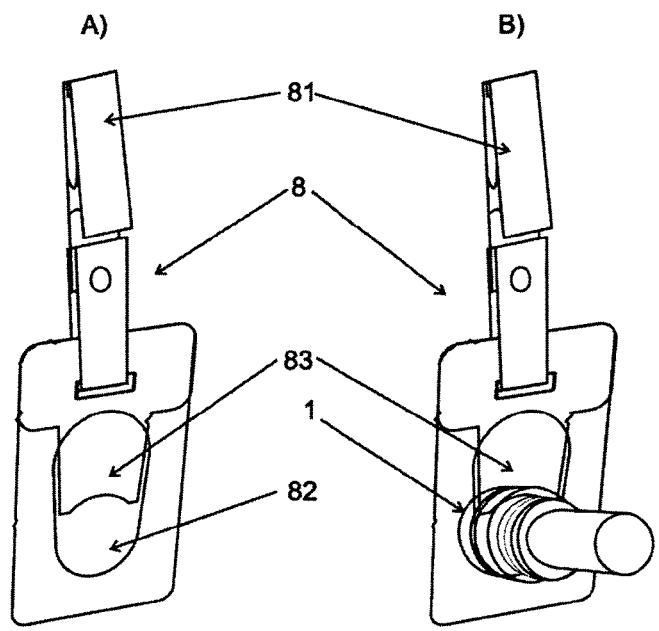
FIGS. 5A and 5B are perspective views of one embodiment of a holder useful in combination with a diffusive sampling device of the invention.

FIG. 5A essentially shows an example of a holder 8 for mobile sampling made e.g. of transparent plastic material, comprising a clip 81 for attaching the holder to a support, e.g. to the clothing of a person. The holder also comprises a hole 82, the dimensions of which allow to attach the sampling device 1 thereto and to secure it with securing flap 83. FIG. 5B shows the same holder 8 with the sampling device attached and the cover removed for sampling.

Experimental Data

The reduction of the dimensions of the devices that actually result from the present invention allow for an easier transportation and technical manipulation than the prior diffusive samplers also provide technical advantages with respect to the performance of other diffusive samplers. This is not the result of an arbitrary scale reduction of other diffusive samplers; rather it implies a completely original concept taking into account critical diffusion parameters to optimize performance, the assembly of different elements inside the device, the characteristics of the building material, the fitting of the different components, porosities, air-tightness conditions, etc.

The reduction of the dimension itself implies further benefits to the device performance; in fact, the lower amount of adsorbent (around 35 mg for a typical graphite charcoal 40-60 mesh) is associated with lower blank levels. This implies higher sensitivity and lower detection limits.

A minimum blank noise level of 40 pg/mg of adsorbent (i.e., benzene in carbopack-X) has been estimated in the laboratory. This implies blank levels higher than 10 ng (for benzene) for typical devices such as Radiello or Perkin Elmer (PE) samplers, which is in agreement with bibliographic data and the inventor's experience in the laboratory. On the other hand, the present devices provide blank levels (for benzene) lower than 1 ng.

Table 2 shows the main design parameters of the most important thermal diffusive samplers on the market compared to sampling device described herein. The small dimensions of herein presented devices (compatible with a lower amount of adsorbent) provide lower blanks and relatively higher sampling rates. Indeed, the ratio blank/uptake mass for the devices of the invention (referred to as "Pods" below) is the lowest, which indicates the highest sensitivity. Pods shows 6.6% of blank level with respect to the uptake amount of benzene after exposure to 1 µg/m³ for 24 hours. For Radiello the expected blank level is already ¼ of the sampled amount, whilst the amount collected by PE is under the detection limit. Another parameter to note is the ratio (Diffusive–Adsorbent) volume/Adsorbent Area, which is a good indication of trapping efficiency (interesting to avoid back diffusion). Pods show the lowest value, which represents the highest efficiency.

TABLE 2

Design parameters and performance characteristic for Radiello, Perkin Elmer and Pods

|  | Radiello | Perkin Elmer | Pods |
|---|---|---|---|
| External diameter, cm | 1.60 | 0.48 | 0.80 |
| Adsorbent-diffusive length, cm | 4.70 | 4.00 | 1.20 |
| Diffusion length, cm | 0.00 | 1.42 | 0.20 |
| Adsorbent length, cm | — | 4.00 | 1.20 |
| Adsorbent diameter, cm | 0.40 | 0.00 | 0.30 |
| Porous membrane thickness, cm | 0.55 | — | 0.20 |
| Adsorbent volume, cm³ | 0.59 | 0.72 | 0.08 |
| Adsorption area, cm² | 5.91 | 0.18 | 1.20 |
| Adsorbent mass, mg | 243.70 | 298.67 | 35.00 |
| Estimated Sampling Rate, cm³/min | 28.24 | 0.63 | 14.73 |
| Adsorbent mass (mg)/SR (cc/min) | 8.63 | 470.62 | 2.38 |
| Diffusive volume, cm³ | 9.45 | 0.98 | 0.60 |
| (Diffusive – Adsorbent) volume/Adsorbent Area, (cm) | 1.50 | 1.42 | 0.43 |
| Blank level (of benzene), ng | 9.75 | 11.95 | 1.40 |
| Uptake benzene mass (24 h at 1 µg/m3), ng | 40.67 | 0.91 | 21.21 |
| Blank/Uptake mass (24 h at 1 µg/m³), % | 23.97 | 1307.28 | 6.60 |

*Estimations based on the diffusion sampling of benzene with a porosity of 20% for the porous membrane.

A man skilled in the art may think that it would be enough to shorten the Radiello or PE adsorbent length until the amount of adsorbent inside reduces to values that provide limited blank levels (i.e. 35 mg) and a smaller device as well. If this is done, what happens is that an overall improvement will not occur because there are other factors that enter the equation. Additional modifications are required to lead to an improvement in performance; these are not obvious to a skilled person in the field and altogether justify the inventive step in the concept.

Table 3 shows the above design parameters and performance characteristics when arbitrary modifications of PE or Radiello design are applied, for instance, by shortening the absorbent length (a) of Radiello to Pods' dimension, (b) of Radiello to get the same amount of adsorbent as Pods, (c) of PE to get the same amount of adsorbent as Pods, direct scaling of Radiello to (d) Pods diameter or to 1 Pods adsorbent length.

TABLE 3

Design parameters and performance characteristics for modified versions of Radiello or Perkin Elmer.

|  | Radiello A | Radiello B | PE C | Radiello D | Radiello E |
|---|---|---|---|---|---|
| External diameter, cm | 1.60 | 1.60 | 0.48 | 0.80 | 0.41 |
| Adsorbent-diffusive length, cm | 1.20 | 0.68 | 0.00 | 2.35 | 1.20 |
| Diffusion length, cm | 0.00 | 0.00 | 1.42 | 0.00 | 0.00 |
| Adsorbent length, cm | 0.00 | 0.00 | 0.47 | 0.00 | 0.00 |
| Adsorbent diameter, cm | 0.40 | 0.40 | 0.00 | 0.20 | 0.10 |
| Porous membrane thickness, cm | 0.55 | 0.55 | 0.00 | 0.28 | 0.14 |
| Adsorbent volume, cm² | 0.15 | 0.08 | 0.00 | 0.07 | 0.01 |
| Adsorption area, cm² | 1.51 | 0.85 | 0.18 | 1.48 | 0.39 |
| Adsorbent mass, mg | 62.22 | 35.00 | 35.00 | 30.46 | 4.06 |
| Estimated Sampling Rate, cm³/min | 7.21 | 4.63 | 0.63 | 14.12 | 9.04 |
| Adsorbent mass (mg)/SR (cm³/min) | 8.63 | 7.56 | 55.15 | 2.16 | 0.45 |
| Diffusive volume, cm³ | 2.41 | 1.36 | 0.34 | 1.18 | 0.16 |
| (Diffusive – Adsorbent) | 1.50 | 1.50 | 1.89 | 0.75 | 0.38 |

TABLE 3-continued

Design parameters and performance characteristics for modified
versions of Radiello or Perkin Elmer.

| | Radiello A | Radiello B | PE C | Radiello D | Radiello E |
|---|---|---|---|---|---|
| volume/Adsorbent Area, (cm) | | | | | |
| Blank level (of benzene), ng | 2.49 | 1.40 | 1.40 | 1.22 | 0.16 |
| Uptake benzene mass (24 h at 1 µg/m$^3$), ng | 10.38 | 6.66 | 0.91 | 20.34 | 13.01 |
| Blank/Uptake mass (24 h at 1 µg/m$^3$), % | 23.97 | 21.01 | 153.20 | 5.99 | 1.25 |

* Estimations based on the diffusion sampling of benzene with a porosity of 20% for the porous membrane As can be seen from Table 3, options A, B and C do not provide a better performance in sensitivity (see ratio Blank/uptake, mass %) with respect to Pods. Pods sensitivity is reached by option D. Nevertheless, the (Diffusive–Adsorbent) volume/Adsorbent Area, (cm), which improves efficiency is still lower (almost half) in the Pods; on the other hand this possibility implies an adsorbent diameter of 2 mm and 2.35 mm length, which is very difficult to manufacture and manipulate. Option E shows design parameters and properties out of the operative range, i.e. minimum adsorbent mass (4 mg) and adsorbent diameters of 1 mm. It is obvious that the overall concept of the Pods provides an overall performance that is superior to other diffusive samplers in terms of sensitivity and efficiency.

Sampling Rates Porosity, Reproducibility, Concentration and Temperature Effect

The diffusive samplers of the invention (Pods) were tested in field and laboratory conditions to study reproducibility and determine sampling rates under different conditions of temperature, concentration level and humidity. The results of this series of experiment are described below.

The Pods were studied for a sampling period of 24 hours. For these tests the selected adsorbent was Carbopack-X 40-60 mesh and the compounds under consideration were aliphatic and aromatic compounds (i.e. pentane, heptane, octane, benzene and toluene). Standards conditions were defined for 20° C., 50% relative humidity, 0.5 m/s of wind speed and concentrations related to the ambient air limit value for benzene (5 µg/m$^3$), 5 samplers for each porosity were tested simultaneously.

Diffusion Body and Temperature Effect

Figure 6:
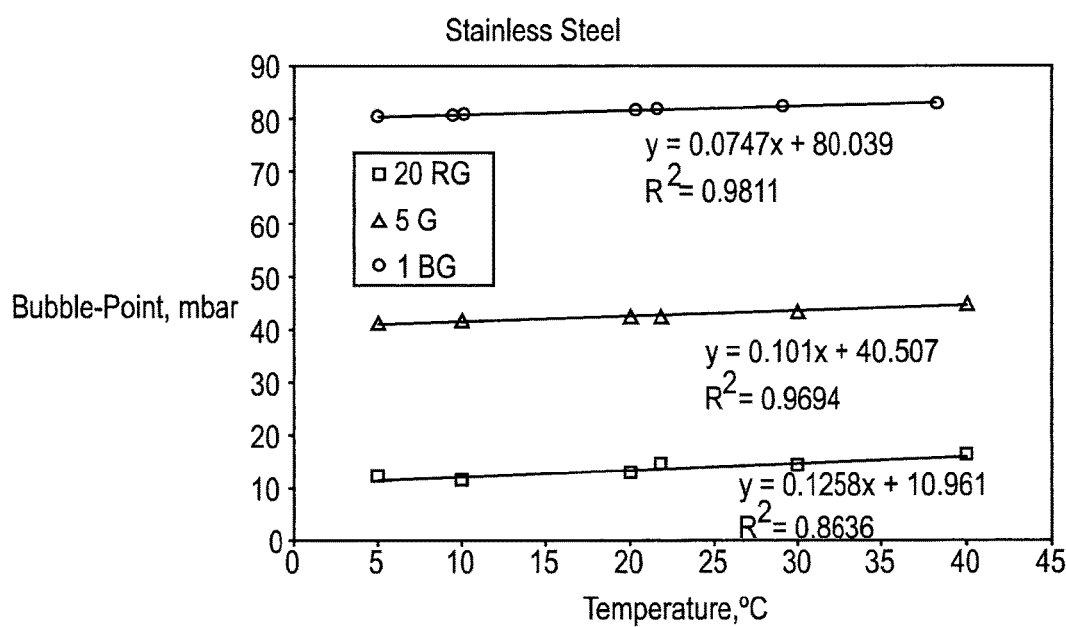
FIG. 6 is graph representing the variation of the bubble point with the temperature for different diffusion bodies in stainless steel.

The bubble point provides an indication of the size of the apparently largest pore. For porous metals an increase of the bubble-point with temperature was observed (See FIG. 6.—Variation of the bubble point with the temperature for different diffusion bodies in stainless steel). This implies a subsequent reduction of the porous size with the increase in temperature. This effect is particularly relevant for diffusion bodies in metal (stainless steel or bronze), whilst PTFE bodies do not show such an important variation.

In case of diffusion, the increase of temperature will reduce the diffusion rate due to the decrease in the porous size. This is an interesting effect as it compensates the increase in diffusivity with temperature and minimizes the overall effect of the temperature in the diffusion process.

These observations were taken into account both 1) in the concept of the new device by minimizing the free air length of diffusion and limiting the control of the diffusion to the porous medium, 2) in the final selection of the material as a diffusion body (e.g. preferably stainless steel or bronze).

The low effect of the temperature on the diffusion process and, consequently, on the sampling rate was tested in the laboratory by determining the sampling rates of some compounds, when the device was operating with diffusion bodies of different pore sizes (1, 5 and 20 µm) and controlled conditions of exposure (24 h sampling time, constant ambient air concentration, wind velocities of 05 m/s and temperatures ranging from 40° C. to −30° C.). Table 4 shows the main results of these experiments, where the low coefficient of variation between the different sampling rates determined between 40° C. to −30° C. is noted

TABLE 4

Median sampling rates for different compounds and diffusion body pore sizes in the range of 40° C. to −30° C. and overall coefficient of variation

| Compound | Pore size* | Median sampling rate from −30° C. to 40° C., µg/m$^3$ | Overall Coefficient of Variation, % |
|---|---|---|---|
| Pentane | 20 GR | 8.07 | 5.92 |
| | 5 GB | 5.18 | 5.06 |
| | 1 BG | 2.32 | 5.06 |
| Benzene | 20 GR | 9.02 | 4.04 |
| | 5 GB | 5.81 | 7.74 |
| | 1 BG | 2.51 | 6.15 |
| Toluene | 20 GR | 7.53 | 8.26 |
| | 5 GB | 4.64 | 7.95 |
| | 1 BG | 2.07 | 6.49 |
| Octane | 20 GR | 5.51 | 12.6 |
| | 5 GB | 3.58 | 13.1 |
| | 1 BG | 1.60 | 8.26 |

*Pore size and color code according to table 1

Reproducibility Under Field Conditions

Test under field conditions showed extremely good reproducibility when several diffusive samplers were exposed simultaneously on the same spot.

Figure 7:
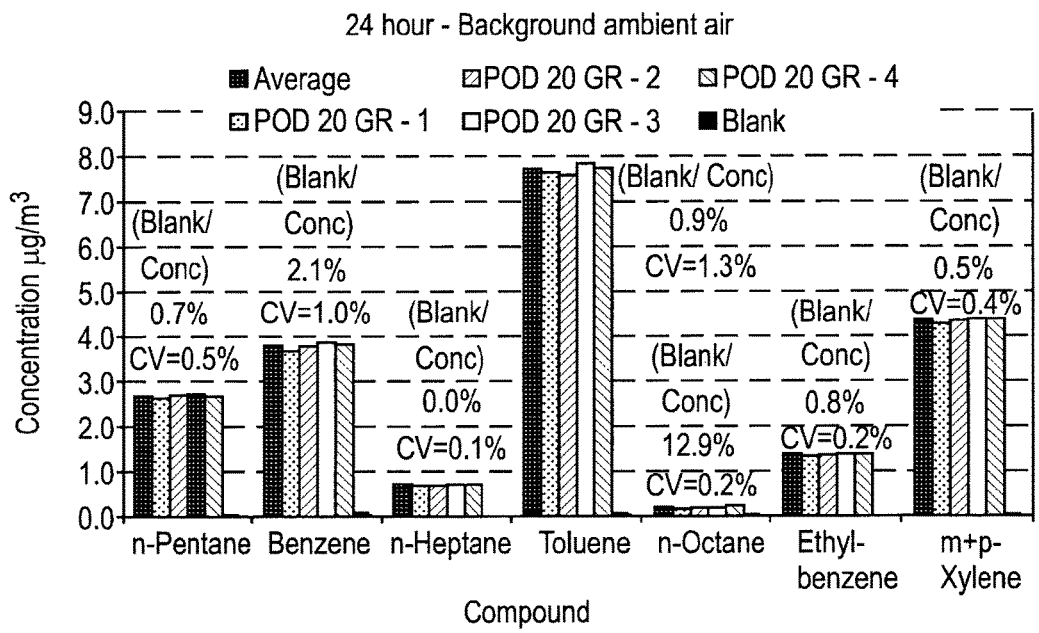
FIG. 7 is graph representing a field experiment for a diffusion sampler 20 GR porosity diffusion body.

FIG. 7 shows the results of exposure to ambient air conditions of four diffusive samplers during 24 hours. In this figure it is also possible to observe the blank levels with respect to the detected concentration, which remained very low and were only significant for n-octane (12% of the quantified levels), but the levels of n-octane were extremely 3 low at about 220 pg/m.

Concentration Level

Figure 8:
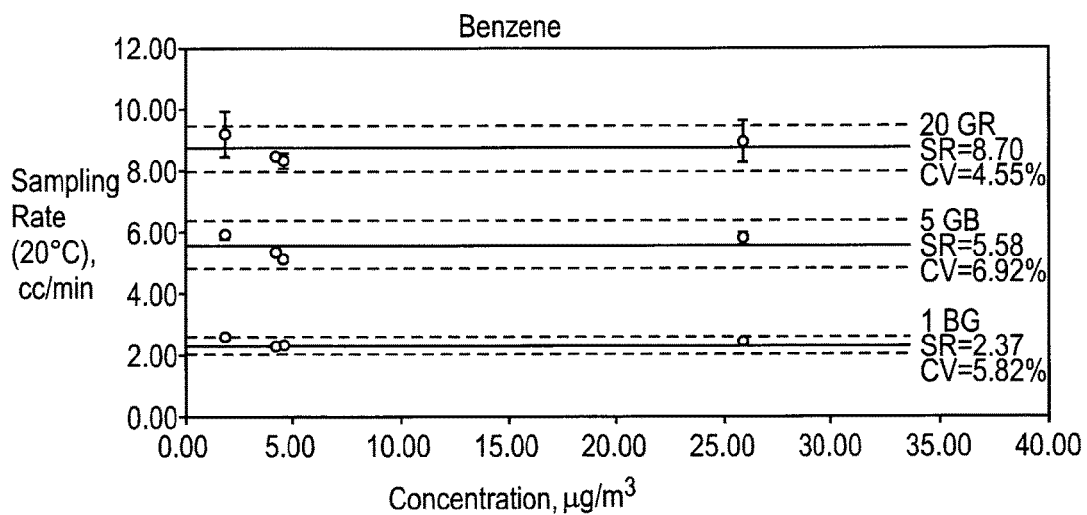
FIG. 8 shows a series of graphs representing the sampling rate at different concentration levels.
Figure 8:
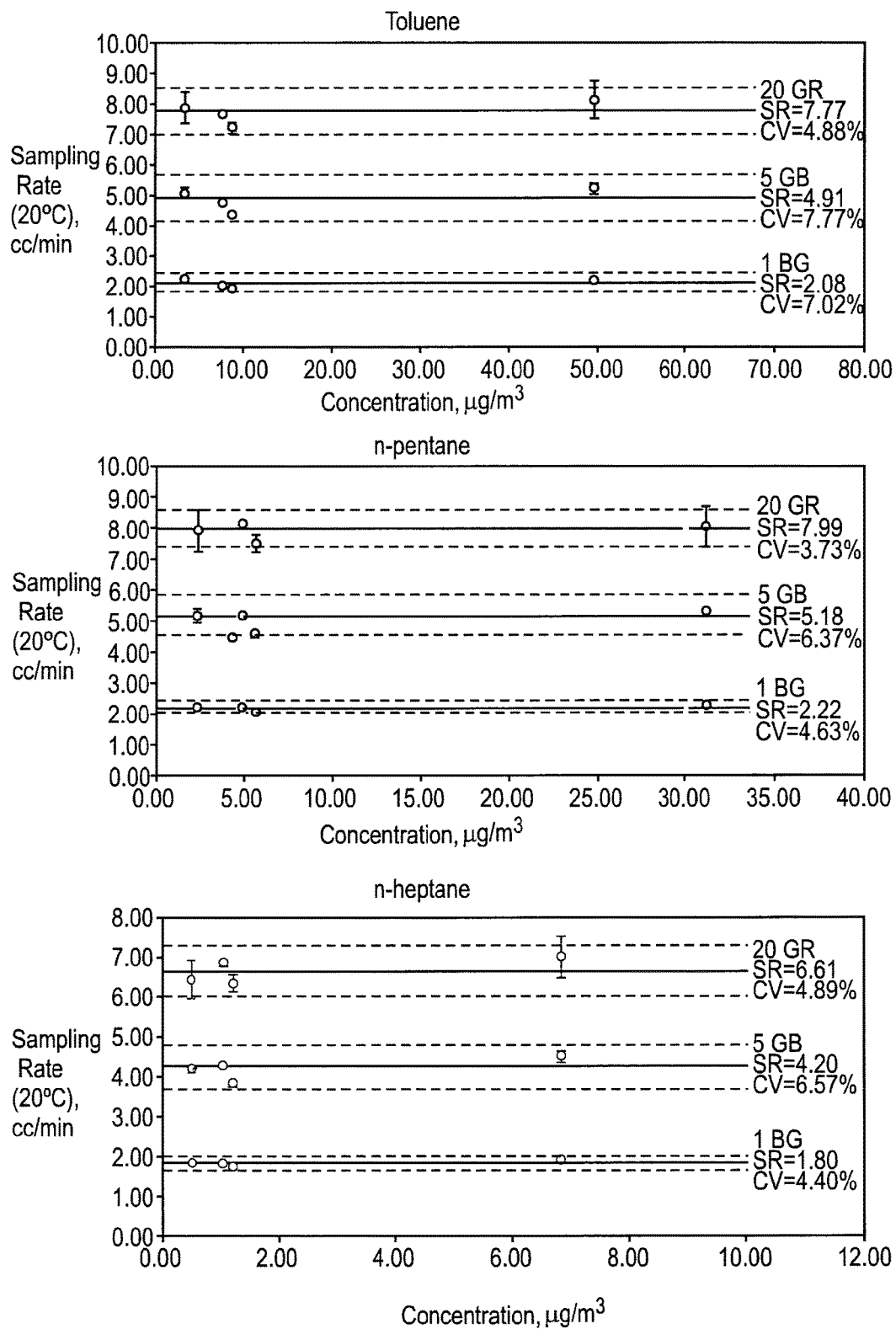
Figure 8:
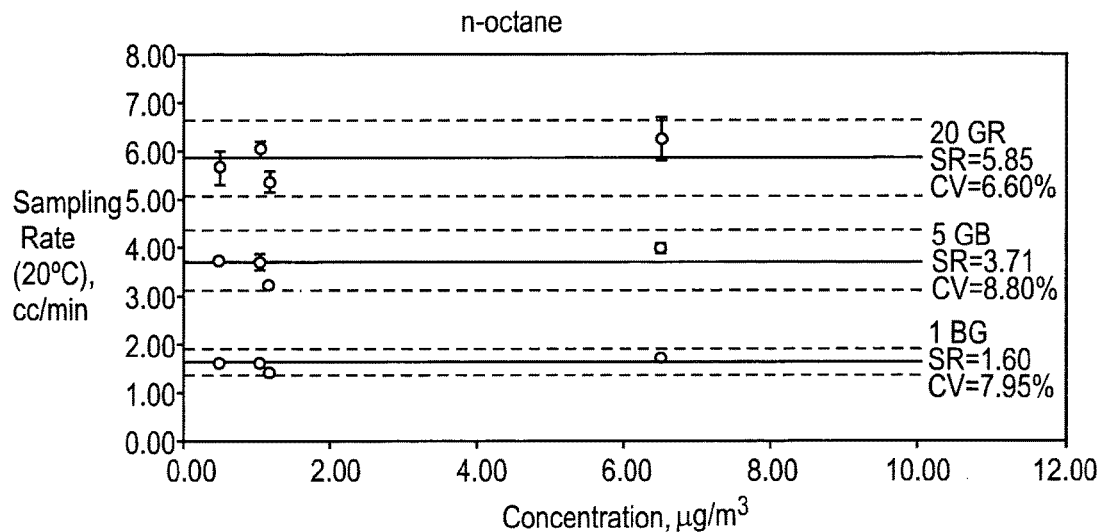

Diffusive samplers of different porosities were exposed during 24 hours at different concentration levels to check the concentration effect on the sampling rate. FIG. 8 shows the results of these tests for the considered compounds. The influence of the concentration on the sampling rate for the studied range of each compound can be considered negligible. In light of these results, it is expected that the system will be able to operate at longer sampling times (weeks) without having an effect on the sampling rate, in particular for the diffusion body that provides the lower sampling rate.

Sampling Rate and Diffusivity

Figure 9:
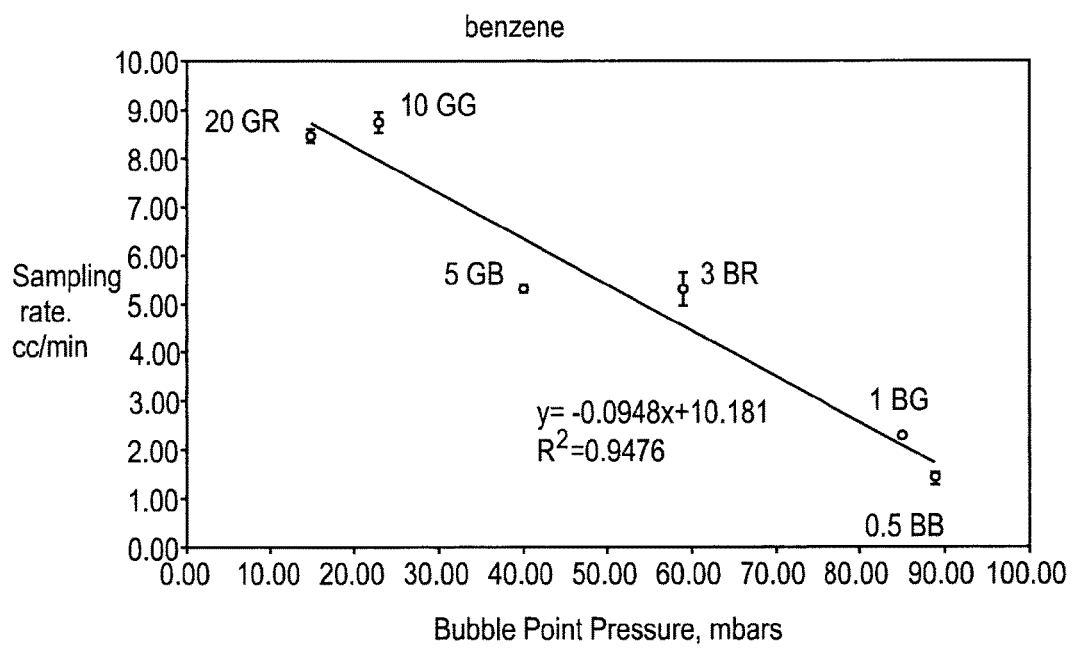
FIG. 9 shows a series of graphs the sampling rates and porosity for different compounds.
Figure 9:
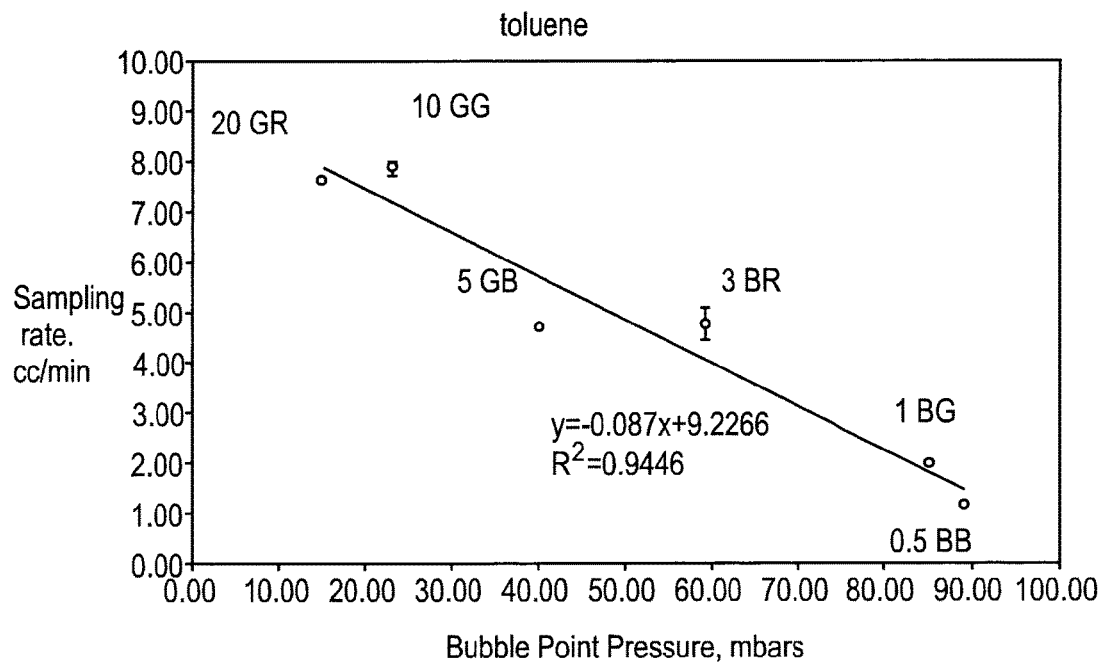
Figure 9:
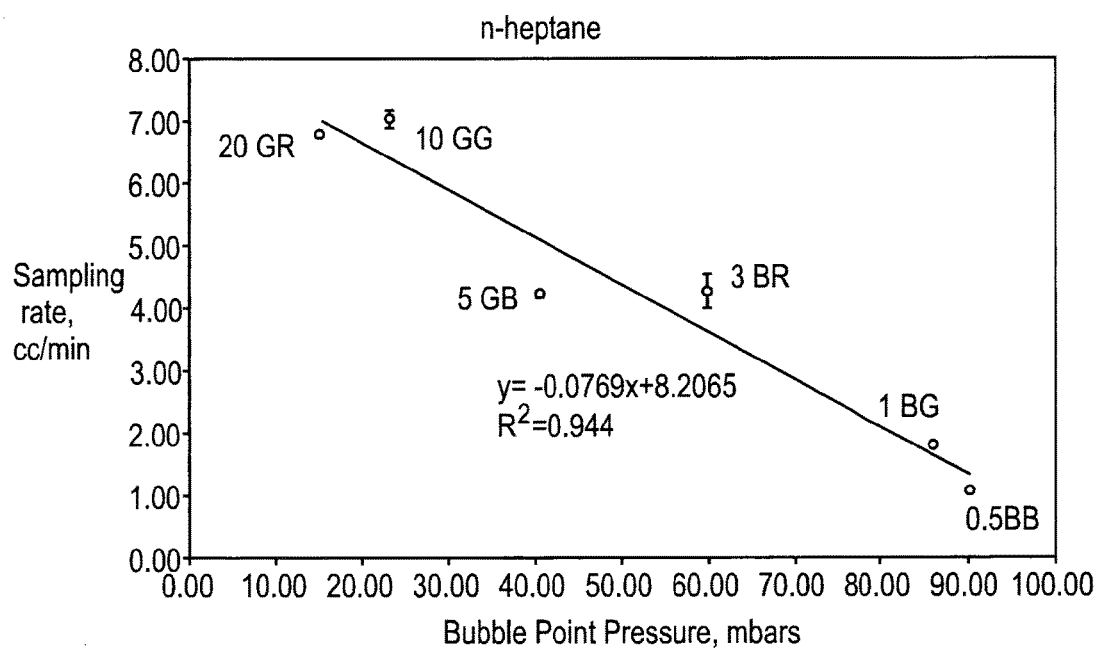
Figure 9:
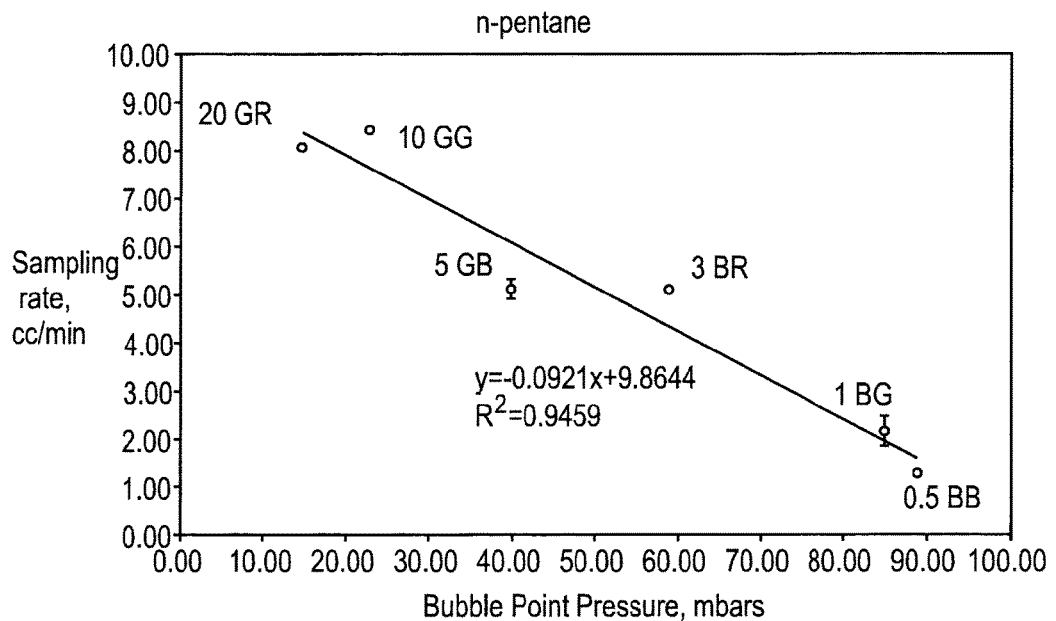
Figure 9:
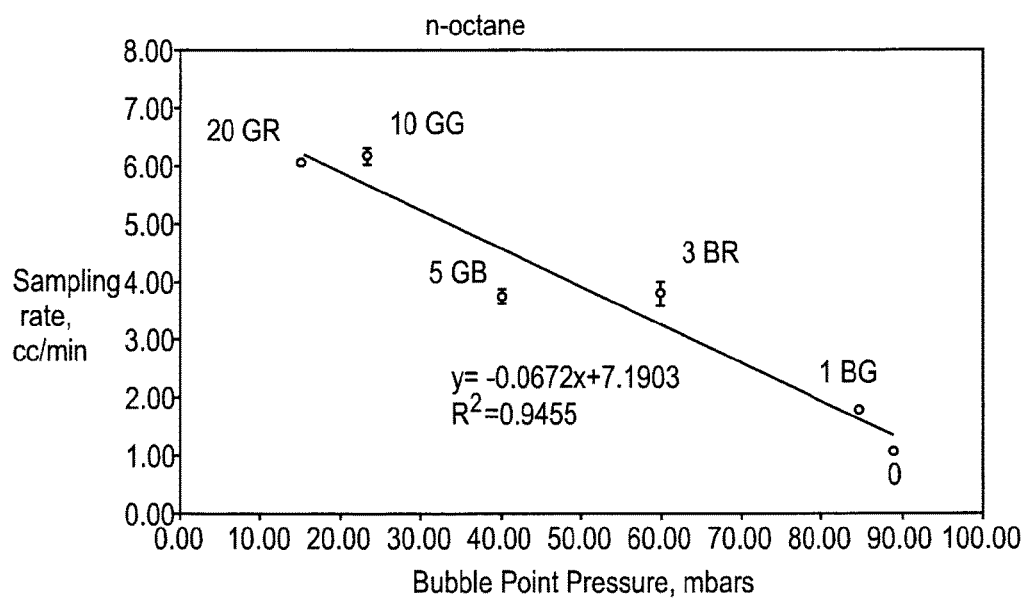

A series of experiments were carried out in order to determine the relationship between sampling rate and porosity (in terms of bubble point). Five diffusive samplers of each porosity from 0.5 to 20 porous size were exposed by quintuplicating in a controlled laboratory test chamber for 24 hours at 20° C., 50% RH, 0.5 m/s wind velocity and known concentration of pollutants (pentane, benzene, toluene, octane). The results of this experiment are shown in FIG. 9.

NO$_2$ sampling

A series of experiments have been carried out regarding the measurements of NO$_2$ with the Pods.

For NO$_2$ sampling, the adsorbent is a solution of triethanolamine TEA at 20% (v/v) in water, which is imbibed into silica gel (Supelclean™ LC-Silica gel (45 μm particle size)) already introduced in the adsorbent container of the Pod. After exposure, the adsorbent body is extracted with 250 μl of ultrapure water in ultrasonic for 20 min into vial.

For analysis an aliquot of 100 μl is taken to be diluted with another 100 μl of a reactive solution containing sulphanilamide, phosphoric acid and N-1-naphthyl)-ethlyene-diamine-dihydrochloride.

The solution is shaken in a vortex and analyzed after 10-30 minutes by spectrophotometry (absorption at 540 nm). The estimated sampling rate for the 20% porosity stainless steel diffusion is circa 17 cm$^3$.

The experiments have been carried out in the proximity to the limit of detection of the Pods. At this level, it has to be noted that the analytical uncertainties are around 30%. This uncertainty will decrease with the amount of nitrite taken up by the diffusive sampler, becoming close to 1% when sampling NO$_2$ concentrations at 2 ppb for 7 days or 30 ppb for 24 hours.

The detection limit of NO$_2$ concentration in air is circa 0.93 ppb (v/v) for 24 hours of exposure, being sampling reproducibility at this level of around 5%. Tests were varying in time, concentration and humidity. No significant effect of humidity was observed at this range.

Figure 10:
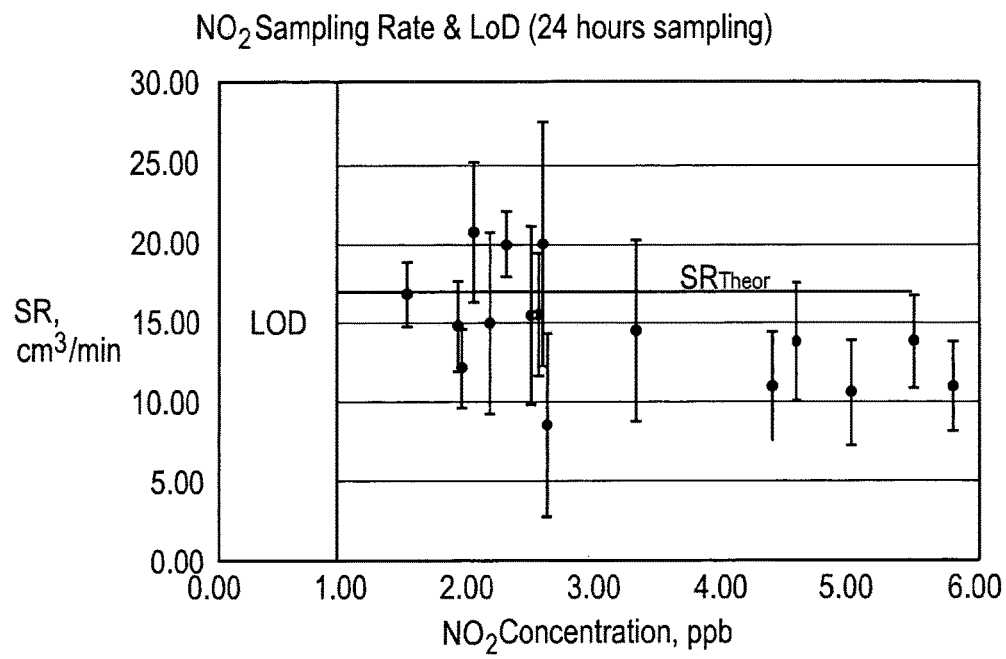
FIG. 10 shows a graph representing $NO_2$ sampling rates for 24 hours of exposure.

The results obtained are shown in FIG. 10. The sampling rates (SR) are expressed in cm$^3$/min and the concentrations of NO$_2$ are expressed in ppb. These results are very satisfying and are even better than the most popular NO$_2$ diffusion sampler known as Palmes diffusion tube. Indeed, Palmes diffusion tube needs at least one week sampling to get such sensitivity (J Environ Monit. 2005 February; 7(2): 169-74. Epub 2005 Jan. 19. Modelling of the uptake rate of the nitrogen dioxide Palmes diffusive sampler based on the effect of environmental factors. Buzica D, Gerboles M, Amantini L, P. Perez Ballesta, De Saeger E).

Polycyclic Aromatic Hydrocarbons (PAHs) Sampling

PAHs are potent atmospheric pollutants which refer to fused aromatic rings and do not contain heteroatoms or carry substituents, for example: Naphthalene, Acenaphthylene, Acenaphthene, Fluorene, Phenanthrene, Anthracene, Fluoranthene and Pyrene. The device according to the present invention has been used for sampling PAHs.

Estimated sampling rates from 5 to 9 cm$^3$/min allow detection of ambient air concentration (ppt) levels in only three days sampling with Brass diffusion bodies. The method involved the use of appropriated adsorbent such as tenax TA, tenax GR, zeolites or XAD. Analyses have been carried out by thermal desorption, gas chromatography separation and mass spectrometry detection.

The results of the tests show a much higher sensitivity compared to the well-known PAH diffusive sampler based on PUF disks, which need from 5 to 12 weeks of sampling to quantify ambient air levels. (F. M Jaward et al. Passive air sampling of polycyclic aromatic hydrocarbons and polychlorinated naphthalenes across Europe. Environmental Toxicology and Chemistry, Vol. 23, No. 6, pp. 1355-1364, 2004).

Volatile Organic Compounds (VOCs) Sampling

VOCs measurements have also been realized with the Pods device according to the present invention. These measurements have been compared with those obtained with the well-known canisters.

In fact, VOCs measurements have been carried out with 20% porosity stainless steel body versus canisters for 3 days sampling period in fields conditions. These measurements have been realized in February in Wyoming at an average temperature of −10° C.

For the comparison between the Pods and the canisters, the sampling rates disclosed in table 5 have been used. The sampling rates are expressed in μg/m$^3$.

TABLE 5

| | Sampling rate, cm3/min (−10° C.) (20% porosity diffusion body - Pods |
|---|---|
| Propene | 18.70 |
| iso-butane | 10.84 |
| n-butane | 10.30 |
| iso-Pentane | 8.56 |
| n-Pentane | 8.61 |
| 1,3-Butadiene | 14.94 |
| 1-Pentene | 10.25 |
| Hexane | 7.73 |
| Benzene | 9.27 |
| Toluene | 7.77 |
| Ethyl-benzene | 5.76 |
| n-Octane | 4.68 |
| m,p-Xylene | 4.06 |
| o-Xylene | 3.66 |
| isoprene | 10.04 |
| 2-methyl-pentane | 10.84 |

In particular, the measured compounds were: propene, iso-pentane, n-pentane, 1,3-butadiene, 1-pentene, hexane, 2-methyl-pentane, benzene, toluene, ethylbenzene, m,p-xylene and o-xylene.

Figure 11:
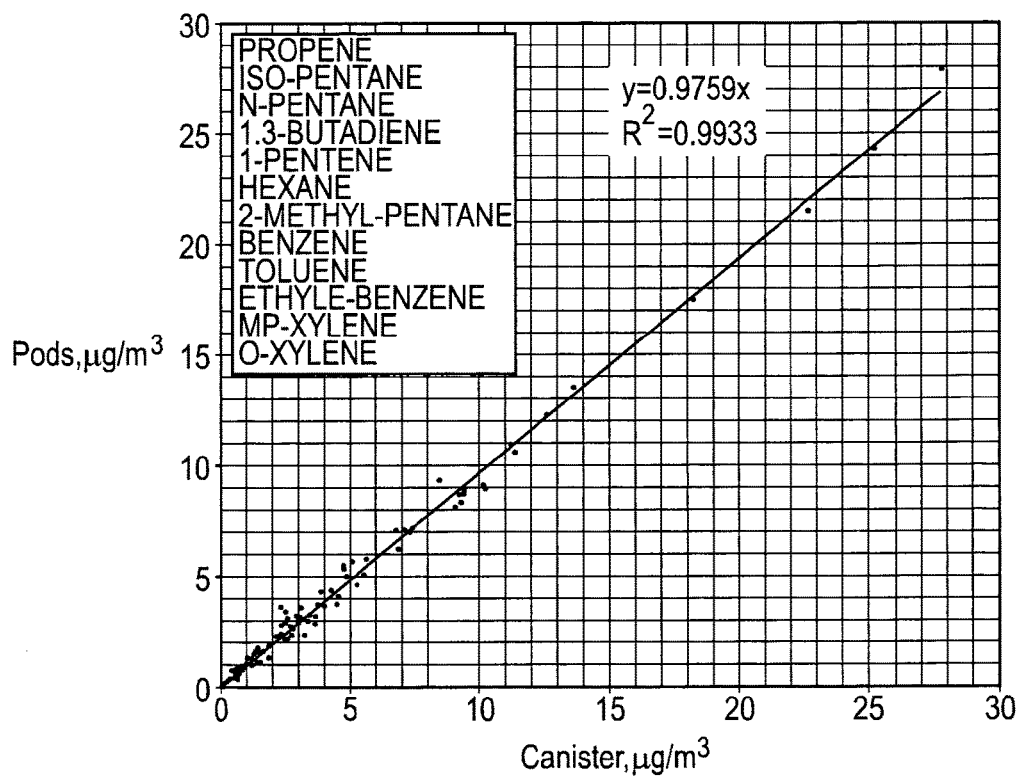
FIG. 11 shows a graph representing the sampling rates of Volatile Organic Compounds (VOCs) of the device of the invention and of a canister.

The results shown at FIG. 11 demonstrate that there is a very good correlation between both techniques concerning the measurement of VOCs.

The invention claimed is:

1. A diffusive sampling device comprising:
a support body;
a porous hollow diffusion body removably held on the support body, the hollow diffusion body having a cylindrically shaped wall with an upper section, comprising a closed upper end, and, a distal lower section, comprising an open lower end;
an adsorbent body located inside the porous hollow diffusion body, the cylindrically shaped wall of the porous hollow diffusion body defining a hollow interior having a length that is greater than a length of the adsorbent body, the adsorbent body being configured for collecting at least one compound to be sampled and analyzed;
one or more o-rings arranged in corresponding grooves located on the distal lower section of the porous hollow diffusion body and configured for holding the porous hollow diffusion body on the support body;
a at least one elastic member disposed inside the porous hollow diffusion body on a surface of the support body and configured for keeping the adsorbent body in a predetermined place inside the upper section of the porous hollow diffusion body;
a cover configured to be removably attached to an upper section of the support body by means of a further o-ring inserted in a further groove arranged on an outer surface of the upper section of the support body, the cover being further configured to match closely an outside shape of the diffusive body to minimize dead volume inside the closed device and to reduce desorption of compounds sampled by the adsorbent body; and
a non-return valve arranged in a top end wall of the cover, the non-return valve being configured for avoiding over-pressure when the cover is attached to the upper section of the support body.

2. The diffusive sampling device as claimed in claim 1, wherein the at least one elastic member comprises a spring.

3. The diffusive sampling device as claimed in claim 1, wherein the porous hollow diffusion body is made of stainless steel, bronze, polytetrafluoroethylene, polypropylene or catalytic materials.

4. The diffusive sampling device as claimed in claim 1, wherein the porous hollow diffusion body has pore diameters from 0.5 to 100 µm.

5. The diffusive sampling device as claimed in claim 1, wherein the adsorbent body is comprised of a mono-block adsorbent.

6. The diffusive sampling device as claimed in claim 1, wherein the adsorbent body is comprised of a particulate adsorbent contained within a perforated container or within a double spring container.

7. The diffusive sampling device as claimed in claim 1, wherein the porous hollow diffusion body has a length from the lower to the upper end of 10 to 30 mm, an outer diameter of 6 to 25 mm and a wall thickness of 1 to 7 mm.

8. The diffusive sampling device as claimed in claim 1, wherein the porous hollow diffusion body has a length from the lower to the upper end of 20.0±0.3 mm, an outer diameter of 8.0±0.3 mm, and a wall thickness of 2.0±0.2 mm.

9. The diffusive sampling device as claimed in claim 1, wherein the support body further comprises a peripheral depression arranged in the raised lower surface and wherein a holder is removably attached to the support body.

10. The diffusive sampling device as claimed in claim 9, wherein the holder is a metal or plastic clip, a screw or a magnetic piece placed at the base of the support body.

11. Use of diffusive sampling device as claimed in claim 1 for passive air monitoring over a large range of time periods.

12. Use of diffusive sampling devices as claimed in claim 1 in stationary, mobile and personal exposure applications.

13. A method for air sampling and monitoring using a diffusive sampling device as claimed in claim 1, wherein the following steps:
   a. placing the diffusive sampling device in a desired stationary or mobile location,
   b. starting the sampling period by removing the cover from the support body,
   c. letting adsorption occur for a determined period of time,
   d. closing the diffusive sampling device by replacing the cover on the support body after said period lapsed,
   e. transferring the closed diffusive sampling device to an analyzing and measuring step comprising the introduction of the adsorbent body into a conventional desorption equipment provided with an analyte detection and measuring device to quantify the analyte(s) adsorbed in the diffusive sampling device.

14. The method as claimed in claim 13, wherein the device is attached in said location using a holder.

15. The method as claimed in claim 13, wherein before effecting step e. the method comprises a sequence of one or more repetitions of steps a-d or b-d.

* * * * *